(12) United States Patent
Ross

(10) Patent No.: US 8,474,771 B2
(45) Date of Patent: Jul. 2, 2013

(54) SURGICAL TRAY METHODS AND APPARATUS

(75) Inventor: Mark W. Ross, Costa Mesa, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 340 days.

(21) Appl. No.: 12/416,025

(22) Filed: Mar. 31, 2009

(65) Prior Publication Data

US 2010/0243590 A1  Sep. 30, 2010

(51) Int. Cl.
*E04G 3/00* (2006.01)
(52) U.S. Cl.
USPC ............... 248/276.1; 248/278.1; 248/282.1; 408/282; 408/408.1; 312/209
(58) Field of Classification Search
USPC ............ 248/276.1, 278.1, 918, 282.1, 284.1; 312/209; 403/162, 227, 282, 154, 408.1; 411/57.1; 16/337, 339, 340, 385
See application file for complete search history.

(56) References Cited

U.S. PATENT DOCUMENTS

| | | | | |
|---|---|---|---|---|
| 2,428,950 A * | 10/1947 | Weiss | | 280/485 |
| RE23,252 E * | 8/1950 | Frazier | | 280/682 |
| 2,698,958 A * | 1/1955 | Adams | | 16/340 |
| 2,935,347 A * | 5/1960 | Liversage | | 403/227 |
| 3,160,379 A * | 12/1964 | Gardella | | 248/125.7 |
| 3,180,655 A * | 4/1965 | Gerner | | 280/93.508 |
| 3,366,430 A * | 1/1968 | Diedrich | | 312/201 |
| 4,610,630 A * | 9/1986 | Betush | | 433/79 |
| 4,620,344 A * | 11/1986 | Lewis, Jr. | | 16/337 |
| 4,695,024 A * | 9/1987 | Haven | | 248/281.11 |
| 6,238,127 B1 * | 5/2001 | Jhumra et al. | | 403/282 |
| 6,736,360 B1 | 5/2004 | Buczek | | |
| 7,007,906 B2 * | 3/2006 | Slatter | | 248/276.1 |
| 7,461,825 B2 * | 12/2008 | Olivera et al. | | 248/282.1 |
| 2008/0067302 A1 | 3/2008 | Olivera et al. | | |

* cited by examiner

*Primary Examiner* — Anita M King
(74) *Attorney, Agent, or Firm* — Abbott Medical Optics Inc.

(57) ABSTRACT

A tray assembly includes an articulatable arm assembly coupled with a tray and selectively held in place by a locking mechanism (e.g., a locking gas spring). A release mechanism coupled with the tray selectively activates and deactivates the gas shock mechanism and is coaxial with and free rotating with respect to an axis of rotation of the tray. The tray may rotate between a horizontal position and a stored position substantially orthogonal to the horizontal position. The arm assembly may include at least one frictional hinge comprising a tapered pin, a tapered bushing in rotational frictional contact with the tapered pin, and an adjustment mechanism coupled to the tapered pin to provide adjustable contact force between the tapered pin and the tapered bushing.

17 Claims, 4 Drawing Sheets

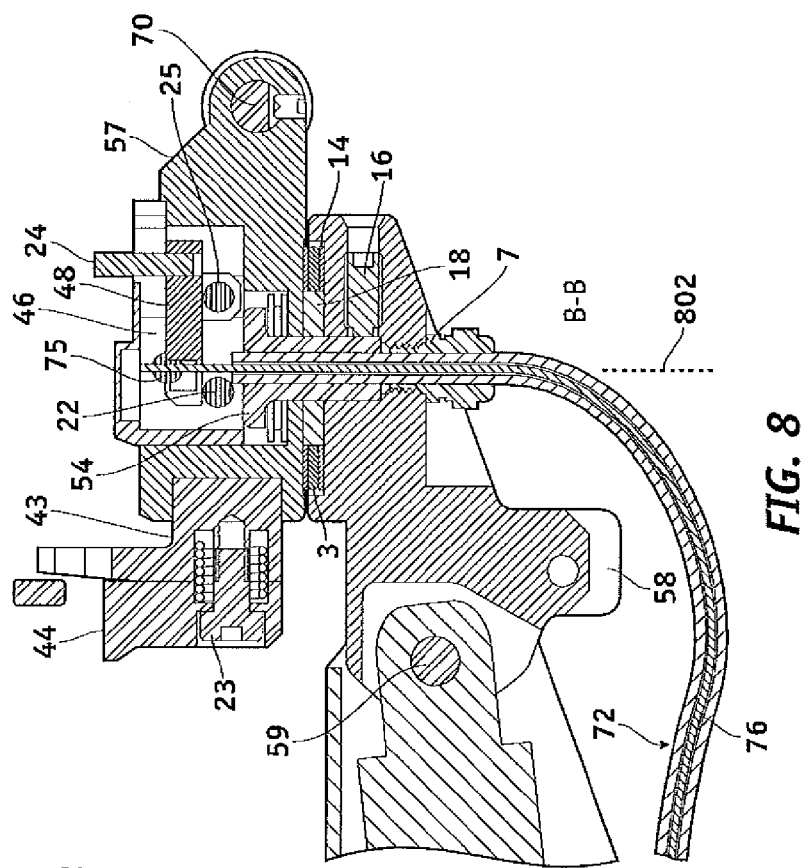
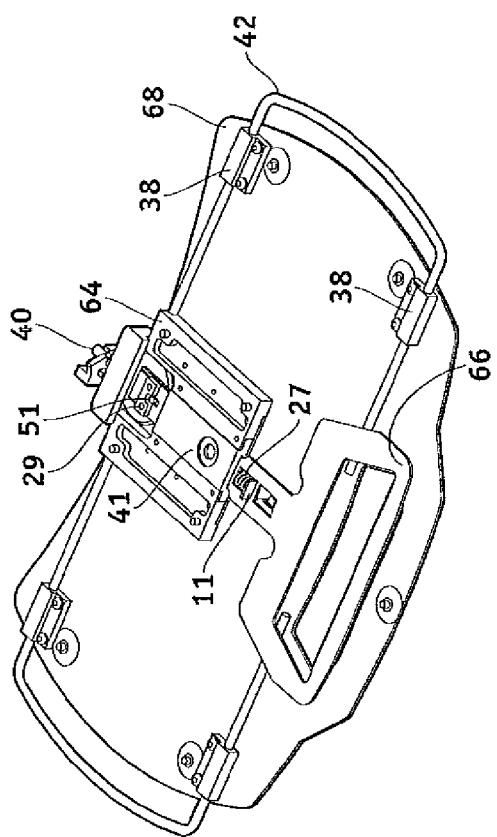
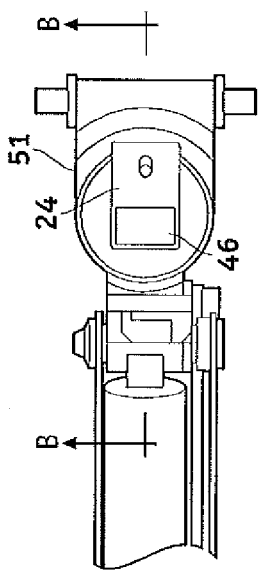

SURGICAL TRAY METHODS AND APPARATUS

TECHNICAL FIELD

The present invention generally relates to surgical tray systems, and more particularly relates to articulatable surgical tray assemblies of the type used in connection with portable surgical consoles.

BACKGROUND

Surgical consoles generally include, among other things, a tray configured to articulate with respect to a console. One or more interconnected arms coupled to the tray are selectively secured in place via a locking mechanism, such as a gas spring or the like. During use, the tray is configured to remain horizontal, and the operator manually engages or disengages the locking mechanism to reposition the arms and tray in the desired position.

Known surgical consoles are unsatisfactory in a number of respects. For example, the use of gas springs typically requires incorporating some form of release mechanism, such as a release cable, between the tray and the gas spring. Such release cables often restrict the movement of the tray and arms, as they cannot generally accommodate a wide range of tray positions, and thus can easily become tangled in the arms and related interconnects.

Furthermore, as conventional tray systems maintain the tray in a generally horizontal position, the storage and transport of such surgical consoles can be difficult, as the tray extends a significant distance outward from the console in an unlocked position. This results in a non-compact and difficult-to-transport configuration.

Moreover, the various hinges and interconnects used in conventional surgical console arm assemblies tend to allow the tray to swing outward with very little resistance, and are often ineffective in keeping the tray in a specific desired location and orientation. In addition, such conventional hinges are subject to hysteresis. That is, they tend to exhibit a lag in response to applied force.

Accordingly, it is desirable to provide articulatable surgical tray assemblies that allow an increased range of motion, can be more easily stored and transported, have improved hinge mechanisms, and incorporate cable release mechanisms that allow for a greater range of tray rotation. Other desirable features and characteristics of the present invention will become apparent from the subsequent detailed description and the appended claims, taken in conjunction with the accompanying drawings and the foregoing technical field and background.

BRIEF SUMMARY

In accordance with one embodiment of the present invention, a tray assembly includes an articulatable arm assembly coupled with a tray and selectively held in place by a locking mechanism (e.g., a locking gas spring). A release mechanism coupled with the tray selectively activates and deactivates the gas shock mechanism and is coaxial with and free rotating with respect to an axis of rotation of the tray.

In accordance with a further embodiment of the present invention, a tray assembly includes an articulatable arm assembly coupled with a tray, wherein the tray is selectively latched to the articulatable arm assembly such that the tray may rotate between a horizontal position and a stored position substantially orthogonal to the horizontal position.

In accordance with a further embodiment of the present invention, a tray assembly includes an articulatable arm assembly coupled with a tray, wherein the arm assembly includes at least one frictional hinge comprising a tapered pin, a tapered bushing in rotational frictional contact with the tapered pin, and an adjustment mechanism coupled with the tapered pin to provide adjustable contact force between the tapered pin and the tapered bushing.

BRIEF DESCRIPTION OF THE DRAWINGS

A more complete understanding of the present invention may be derived by referring to the detailed description and claims when considered in conjunction with the following figures, wherein like reference numbers refer to similar elements throughout the figures.

FIG. 6 is an isometric bottom view of various components of an exemplary tray;

FIG. 7 is a top view of the end of the outer arm assembly;

FIG. 8 is a cross-section through the top view shown in FIG. 7;

DETAILED DESCRIPTION

The following detailed description is merely illustrative in nature and is not intended to limit the invention or the application and uses of the invention. Furthermore, there is no intention to be bound by any expressed or implied theory presented in the preceding technical field, background, brief summary or the following detailed description. The invention may be described herein in terms of functional and/or logical block components and various processing steps. For the purposes of conciseness, conventional techniques and systems related to surgical tray systems, hydraulics, friction hinges and the like are not and need not be described in detail herein.

Figure 1:
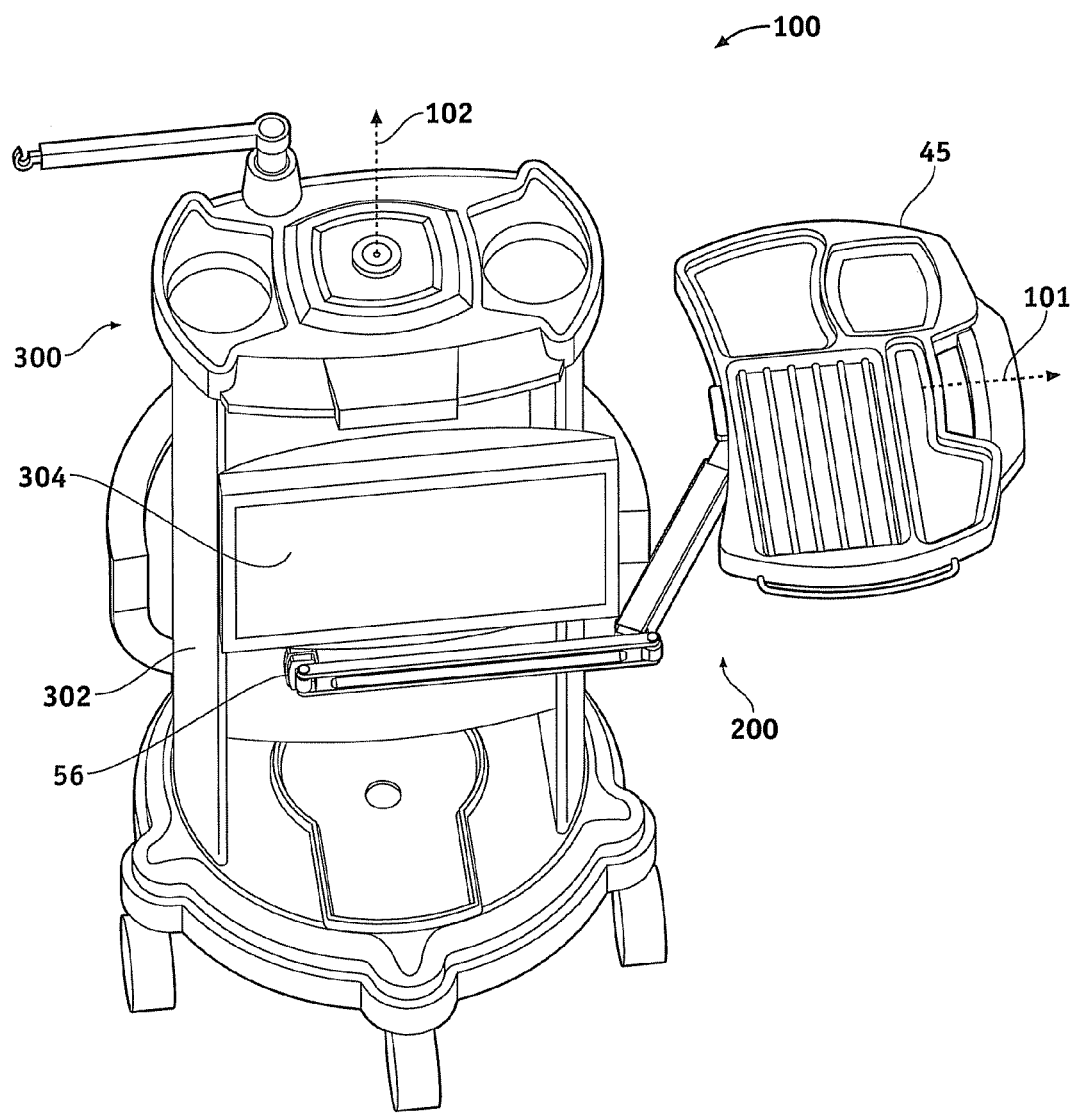
FIG. 1 is an overview of a surgical console system useful in describing the present invention.

Referring now to FIG. 1, a surgical console system 100 in accordance with one embodiment of the present invention generally includes a surgical console 300 having a tray 45 coupled with a console body (or simply "body") 302 via a tray arm 200 having any number of articulating interconnects and linkages as described in further detail below. In this way, tray 45 may be selectively positioned and oriented in space.

A typical surgical console 300 may have a variety of shapes and will generally include a number of subcomponents, drawers, and the like, but in general often contains one or more displays or monitors 304 that generally define a "front"—i.e., a surface or combination of surfaces that are facing an operator in a typical viewing orientation during conventional use. Thus, in the illustrated embodiment, tray arm 200 is coupled with body 302 via a mount 56 that is secured to what would generally be considered the "front" of surgical console 300. Note, however, that the present invention is not limited to any particular size, shape, or configuration of surgical console system, and that the particular system 100 illustrated in FIG. 1 is merely one example useful in describing the present invention.

Typically, tray 45 remains in a horizontal orientation (generally planar and parallel to the floor) to hold various workpieces and tools during use. In accordance with one aspect, however, tray arm 200 and its associated components are configured such that tray 45 may be rotated and folded substantially flat against body 302 of console 300, while tray arm 200 collapses in a compact fashion to facilitate this configuration. A handle or other actuator preferably incorporated into tray 45 is engaged by the operator to release a locking mechanism and to reposition the various illustrated components.

More particularly, unlike prior art systems, tray 45 may be positioned and latched adjacent to body 302 (e.g., the front of body 302) such that tray axis 101 (an axis coplanar with the plane of tray 45 and, in this case, its minor axis) is substantially parallel to the console axis 102—i.e., an axis generally perpendicular to the floor or surface upon which it rests. Such a configuration is advantageous for, inter alia, transport and storage of system 100.

At the same time, tray arm 200 provides tray 45 a wide range of motion such that it may be placed on nearly all sides of body 302 during use (e.g., with reference to FIG. 1, tray 45 extends both to the left and right of the front surface generally defined by monitor 304).

FIGS. 2-5 provide helpful illustrations of an exemplary tray arm 200 in various configurations and from a variety of viewpoints. As shown, tray arm 200 generally includes two assemblies: an inner arm assembly 202 (e.g., the arm assembly more closely linked to the console body) and outer arm assembly 203 (the arm assembly linked to tray 45). Inner arm assembly 202 is linked to the console body (not illustrated) via a suitable mount 56. Furthermore, each of the various linkages are coupled via respective interconnects 210, 212, and 214, which may have a variety of degrees-of-freedom to effect proper movement of tray 45. Arm assemblies 202 and 203 may have any suitable shape, and may be accompanied by various other linkages and other mechanical components known in the art.

Figure 3:
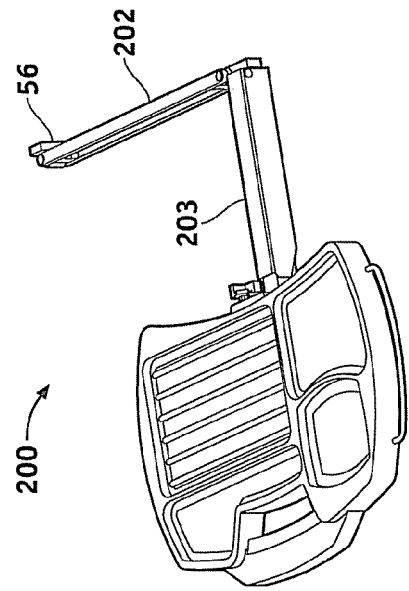
FIGS. 2-5 present various isometric views of a tray and arm assembly in accordance with one embodiment.
Figure 2:
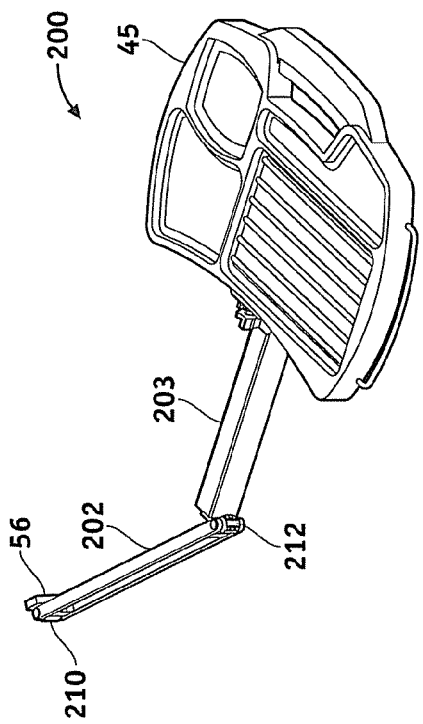
Figure 4:
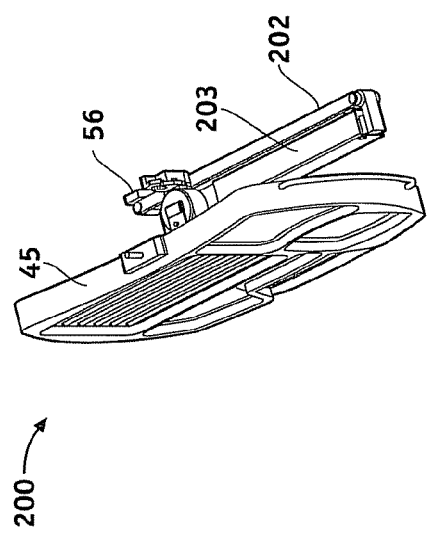

FIGS. 2-4 depict movement of tray arm 200 and tray 45 from an extended position where tray 45 is placed to the left of mount 56 (as viewed in FIG. 2), to a position where inner arm assembly 202 and outer arm assembly 203 are at approximately a 90 degree angle (FIG. 3), to a fully collapsed position where inner arm and outer arm assemblies 202 and 203 are adjacent and oriented 180 degrees with respect to each other, while tray 45 is oriented such that the plane of tray 45 is oriented perpendicular to its typical horizontal orientation during use, allowing it to lie substantially flat vertically adjacent to the console body (not shown). In this position, a latching mechanism allows the tray to be released from its typical horizontal position for storage, where it may be secured by a secondary clip coupled with body 302.

Figure 5:
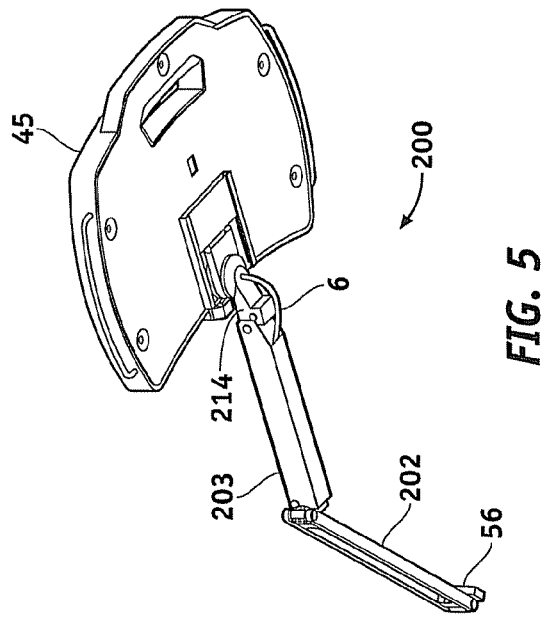

FIG. 5 is an isometric underside view corresponding to the configuration illustrated in FIG. 2. As can be seen from this figure in conjunction with FIGS. 2-4, interconnect 210 between mount 56 and inner arm assembly 202 provides one degree of freedom (i.e., lateral rotation), and interconnect 212 provides two degrees of freedom (lateral rotation accompanied by rotation along an orthogonal axis). Interconnect 214 allows rotation around two axes as well as other features, described in detail below.

A locking mechanism, such as a locking gas shock/spring ("shock") 6, is coupled between interconnects to lock the arm in place and thereby stabilize tray 45, as is known in the art. Such locking gas springs (or "shocks") allow selective locking of the spring in a desired linear position. The present invention is not limited to any particular type or configuration of locking mechanism.

This wide range of motion depicted in the figures is accomplished, in part, through the use of a novel cable release scheme that allows for rotation of tray 45 without tangling the release cable as is typical in prior art systems. In one embodiment, for example, surgical tray 45 includes a handle or other actuator that comes into contact with a pin at the pivot of the tray 45. When the handle is pulled, the pin pivots, causing a connected lever to be raised. The lever is mechanically coupled with the cable such that raising the lever causes the cable to be pulled tight, which releases a valve on the gas shock or otherwise disables the locking mechanism. This allows tray 45 to continue to rotate around the pivot at the interface of the outer arm and the tray.

More particularly, FIGS. 6-8 depict a release mechanism in accordance with an exemplary embodiment. As shown in FIG. 6, the underside of a subsystem within tray 45 generally includes a tray release handle (or simply "handle") 66 coupled with tray bottom panel 68 via a spring mechanism 11. Spring mechanism 11 may include spring 27. Handle 66 is secured within handle guide 41 to constrain movement to spring-loaded translation with respect to panel 68. Handle guide 41 is secured to a tray mount bracket 64, and handle 66 is coupled with lift pin block 51 (which is secured via screws 29) as described below. A tray drape (e.g., wire drape) 42 may be secured to panel 68 via a wire form guide 38, and a tray lock pin 40 is provided for latching during use.

FIG. 7 is a top view of the end of outer arm 203 with the tray removed, and illustrates a cable lift housing 46, pin dowel (or simply "pin") 24, and lift pin block 51. As can be seen, lift pin block 51 allows pin 24 to move laterally within a corresponding slot. A cross-section (B-B) through these components is shown in FIG. 8.

As shown in FIG. 8, a cable release 72 includes a wire 76 that terminates on one end in a ball or bead 75. Wire 76 is threaded through cable lift block 48 such that bead 75 abuts a surface of cable lift block 48, which is provided within a cable lift housing 46. Pin dowel 24 abuts cable lift block 48, which pivots on pin 25. A screw or other stop mechanism 22 restricts rotation of block 48 due to tension applied by bead 75 and wire 76.

Wire 76 (and, in general, a portion of release cable 72) fits within a central bore within hub spindle bolt (or simply "bolt") 54), and extends out through a strain relief component 7. A set screw 16 may be used to secure bolt 54. A washer (e.g., thrust washer) 14, a bearing 3, and a second washer 18 are provided between the rotating components—i.e., swivel 57 and lift hub 58. Thus, as spindle bolt 54 is coaxial with the axis of rotation 802 of swivel 57 with respect to lift hub 58, release cable 72 does not experience tangling during rotation, and therefore the tray (which is coupled with swivel 57 via pivot shaft 70) may be freely rotated 360 degrees. Lift hub 58 rotates with respect to the outer arm via pivot bolt 59.

A tray lock latch 44, torsion spring 43, screw 23 coupled with swivel 57 are used to latch to and position tray 45. In general, this latch can be actuated manually to release tray 45 and allow for storage (e.g., the vertical position shown in FIG. 4). That is, latch 44 selectively engages tray lock pin 40 (FIG. 6) via torsion spring 43.

When tray release handle 66 is actuated (e.g., pulled toward the operator), it causes pin 24 to be rotated slightly (clockwise in FIG. 8) causing the left side of the lever formed by block 48 to be raised. When thus actuated, bead 75 is similarly raised, causing movement of wire 76 within release cable 72, which is coupled with a suitable power shock system (not shown). When block 48 is not raised (i.e., handle 66 is not being actuated), cable 72 is configured such that it is loose enough to allow for complete rotation of the tray. In this way, rotation of swivel 57 is not impeded by release cable 72.

Figure 10:
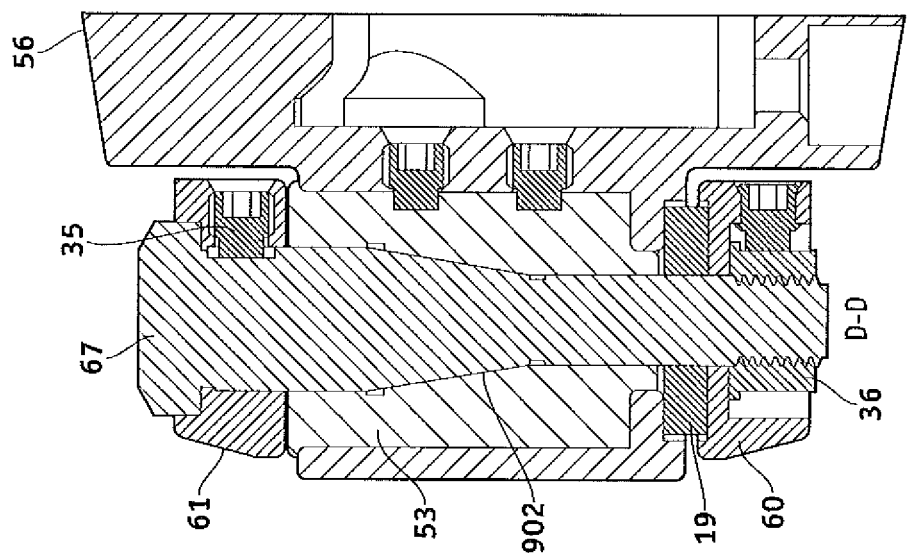
FIG. 10 is a cross-section through the top view shown in FIG. 10.
Figure 9:
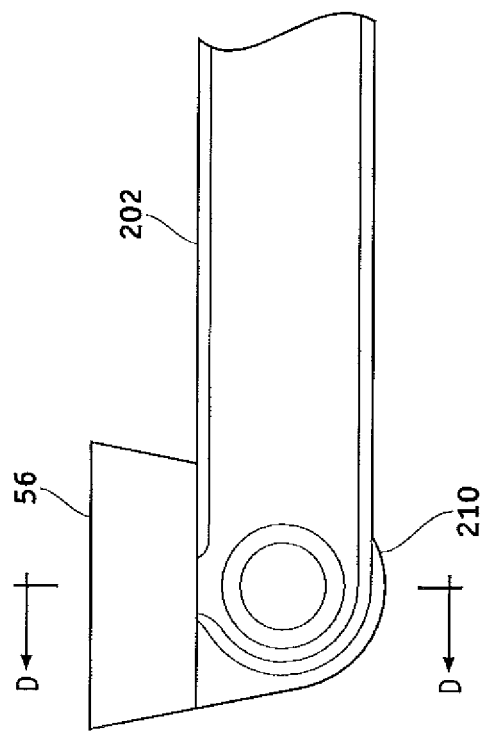
FIG. 9 is a top view of the inner arm and associated mount.

In accordance with another aspect, tray arm 200 incorporates one or more frictional hinges that may be tightened to various degrees without incurring hysteresis in movement. For example, FIG. 9 shows a top view of interconnect 210 between mount 56 and inner arm assembly 202, while FIG. 10 shows a relevant cross-section through this assembly. The frictional hinge illustrated in these figures may also be implemented in any of the other interconnects previously described.

As illustrated, a pivot shaft ("tapered pin," or "shaft") 67 is coaxially inserted within a tapered pin seat (or "tapered bushing") 53, which may comprise any combination of materials sufficient to provide the desired level of friction to inhibit rotation of shaft 67 with respect to mount 56. In one embodiment, pin seat 53 is a Dekin acetal bushing, and shaft 67 is a conventional stainless steel. Tapered pin seat (or "tapered bushing") 53 may comprise a lumen through which the pivot shaft shat 67 may be inserted. A portion of the lumen of the tapered pin seat may be tapered as shown in FIG. 10.

An adjustment nut 36 coupled with one end of shaft 67 secures it to bottom 60 of inner arm 202. The opposite side of shaft 67 seats within top 61 of inner arm 202, and may be secured via one or more set screws 35. A suitable washer 19 is positioned between the bottom 60 of inner arm 202 and inner mount 56.

When inner arm 202 rotates with respect to mount 56, taper pin seat 53 and shaft 67 produce a frictional resistance force whose magnitude can be easily adjusted by tightening or loosening nut 36. That is, tightening nut 36 increases the axial tensile force and consequently the frictional contact force between the two members. The use of a tapered contact area 902 in conjunction with this adjustment mechanism allows the hinge to be tightened without incurring the hysteresis experienced in prior art systems. The degree of taper (or bevel angle) as well as the diameter, size, and shape of the tapered region 902 may be selected to achieve the desired resistance. In one embodiment, for example, the bevel angle is between about 20 and 40 degrees.

While at least one example embodiment has been presented in the foregoing detailed description, it should be appreciated that a vast number of variations exist. It should also be appreciated that the example embodiment or embodiments described herein are not intended to limit the scope, applicability, or configuration of the invention in any way. Rather, the foregoing detailed description will provide those skilled in the art with a convenient road map for implementing the described embodiment or embodiments. It should be understood that various changes can be made in the function and arrangement of elements without departing from the scope of the invention and the legal equivalents thereof.

The invention claimed is:

1. A surgical tray assembly comprising:
a tray defining a tray plane; and
an articulatable arm assembly coupled with the tray and the tray configured to be selectively held at a desired orientation by a locking mechanism coupled to the articulatable arm assembly,
wherein the articulatable arm assembly is configured and dimensioned to couple with a surgical console, and
wherein the articulatable arm assembly includes at least one frictional hinge comprising a tapered pin, a bushing in rotational frictional contact with the tapered pin, and an adjustment mechanism coupled with the tapered pin to provide adjustable contact force between the tapered pin and the bushing,
wherein the bushing comprises a lumen, wherein at least a portion of the lumen is tapered; and
wherein the articulatable arm assembly comprises a first arm having a first end and second end and a second arm having a first end and second end,
wherein the second end of the first arm is coupled with the first end of the second arm by a first interconnect, and the second end of the second arm is coupled with the tray by a second interconnect;
wherein the first interconnect and the second interconnect each comprise a frictional hinge;
wherein the first end of the first arm has a rotational axis; and
wherein the arm assembly allows the tray to be rotated greater than 180 degrees about the rotational axis of the first end of the first arm.

2. The surgical tray assembly of claim 1, wherein the bushing comprises an acetal material.

3. The surgical tray assembly of claim 1, wherein the tapered pin comprises stainless steel.

4. The surgical tray assembly of claim 1, wherein the adjustment mechanism comprises an adjustable nut coupled with one end of the tapered pin.

5. The surgical tray assembly of claim 1, wherein the bushing has a bevel angle of between 20 and 40 degrees.

6. The surgical tray assembly of claim 1, further comprising a release mechanism coupled with the tray and the locking mechanism, wherein the release mechanism is configured to selectively activate and deactivate the locking mechanism, and wherein the release mechanism allows the tray to rotate substantially a full turn within the tray plane about a tray rotational axis.

7. The surgical tray assembly of claim 6, wherein the locking mechanism comprises a locking gas spring.

8. The surgical tray assembly of claim 7, wherein locking gas spring is coupled with the tray via a release cable that connects to the tray coaxially with respect to the tray rotational axis.

9. The surgical tray assembly of claim 8, wherein tray includes tray release handle coupled with the release cable.

10. The surgical tray assembly of claim 1, wherein the at least a portion of the lumen that is tapered is linear.

11. A surgical tray console, comprising:
a console body;
a tray defining a tray plane;
an articulatable arm assembly coupled between the tray and the console body, wherein the tray is configured to be selectively held at a desired height by a locking mechanism coupled with the articulatable arm assembly;
a release mechanism coupled with the tray and the locking mechanism, wherein the release mechanism is configured to selectively activate and deactivate the locking mechanism, and wherein the release mechanism allows the tray to rotate substantially a full turn within the tray plane about a tray rotational axis; and
an actuatable latch mechanism coupled with the articulatable arm assembly and the tray, wherein the actuatable latch mechanism and the articulatable arm assembly are configured to allow the tray to be selectively moved to a stored position such that the tray plane is substantially orthogonal to a horizontal position;
wherein the articulatable arm assembly comprises a first arm having a first end and second end and a second arm having a first end and second end;
wherein the first end of the first arm is coupled with the console body, the second end of the first arm is coupled with the first end of the second arm by a first interconnect, and the second end of the second arm is coupled with the tray by a second interconnect;

wherein the first interconnect and the second interconnect each comprise a frictional hinge;

wherein at least one frictional hinge comprising a tapered pin, a bushing in rotational frictional contact with the tapered pin, and an adjustment mechanism coupled with the tapered pin to provide adjustable contact force between the tapered pin and the tapered bushing, wherein the bushing comprises a lumen, wherein at least a portion of the lumen is tapered;

wherein the first end of the first arm has a rotational axis; and wherein the arm assembly allows the tray to be rotated greater than 180 degrees about the rotational axis of the first end of the first arm.

12. The surgical tray console of claim 11, wherein the locking mechanism comprises a locking gas spring, wherein the locking gas spring is coupled with the tray via a release cable that connects to the tray coaxially with respect to the tray rotational axis.

13. The surgical tray console of claim 11, wherein, in the stored position, at least one of the tray and the outer arm is releasably secured to the console body.

14. The surgical tray console of claim 11, wherein:

the articulatable arm assembly comprises an inner arm having a first end and a second end; and an outer arm having a first end and a second end, wherein the second end of the inner arm is coupled with the first end of the outer arm by a first interconnect, and the second end of the outer arm is coupled with the tray by a second interconnect;

wherein the first interconnect and the second interconnect each comprise a frictional hinge, and wherein, in the stored position, the inner arm and the outer arm are adjacent and substantially parallel.

15. The surgical tray assembly of claim 11, wherein the at least a portion of the lumen that is tapered is linear.

16. A surgical tray assembly comprising:

a tray defining a tray plane; and an articulatable arm assembly coupled with the tray and the tray configured to be selectively held at a desired orientation by a locking mechanism coupled to the articulatable arm assembly, wherein the articulatable arm assembly is configured and dimensioned to couple with a surgical console, and wherein the articulatable arm assembly includes at least one frictional hinge comprising a tapered pin, a bushing in rotational frictional contact with the tapered pin, and an adjustment mechanism coupled with the tapered pin to provide adjustable contact force between the tapered pin and the bushing, wherein the bushing comprises a lumen, wherein at least a portion of the lumen is tapered wherein the articulatable arm assembly comprises:

an inner arm having a first end and a second end; and an outer arm having a first end and a second end;

wherein the second end of the inner arm is coupled with the first end of the outer arm by a first interconnect, and the second end of the outer arm is coupled with the tray by a second interconnect, wherein the first interconnect and the second interconnect each comprise a frictional hinge;

wherein the first interconnect has two degrees of freedom;

wherein the first end of the inner arm has a rotational axis; and wherein the arm assembly allows the tray to be rotated greater than 180 degrees about the rotational axis of the first end of the inner arm.

17. The surgical tray assembly of claim 16, wherein the locking mechanism is coupled between the first end and the second end of the outer arm.

* * * * *